United States Patent [19]

Fedotov et al.

[11] Patent Number: 4,596,351
[45] Date of Patent: Jun. 24, 1986

[54] SURGICAL STAPLING APPARATUS

[75] Inventors: Vladimir M. Fedotov; Vladimir P. Kharchenko, both of Moscow; Iosif L. Lipovsky, Leningrad; Tatyana L. Ivanova, Moscow, all of U.S.S.R.

[73] Assignee: Vsesojuzny Nauchno-Issledovatelsky I Ispytatelny Institut Meditsinskoi Tekhniki, Moscow, U.S.S.R.

[21] Appl. No.: 641,681

[22] Filed: Aug. 17, 1984

[30] Foreign Application Priority Data

Aug. 19, 1983 [SU] U.S.S.R. .............................. 3649473

[51] Int. Cl.⁴ ............................................. A61H 17/00
[52] U.S. Cl. .................................. 227/19; 128/334 R; 227/DIG. 1
[58] Field of Search ............... 128/334 R, 334 C, 335; 227/DIG. 1, 19, 135

[56] References Cited

U.S. PATENT DOCUMENTS

| | | | |
|---|---|---|---|
| 3,078,465 | 2/1963 | Bobrov | 227/DIG. 1 |
| 3,079,606 | 3/1963 | Bobrov et al. | 227/DIG. 1 |
| 3,315,863 | 4/1967 | O'Dea | 227/DIG. 1 |
| 3,490,675 | 1/1970 | Green et al. | 227/DIG. 1 |
| 4,290,542 | 9/1981 | Fedotov et al. | 277/155 |

OTHER PUBLICATIONS

"Shaping of Metal Stitches", *Surgical Suturing Apparatus*, Edition VII, Vniikhai, Moscow, 1967, pp. 13-18, (w/translation).

*Primary Examiner*—Paul A. Bell
*Attorney, Agent, or Firm*—Fleit, Jacobson, Cohn & Price

[57] ABSTRACT

A surgical stapling apparatus, comprising a thrust case incorporating a lengthwise groove. Said groove accommodates a magazine containing staples, and drivers of the staples, and a wedge interacting with said pushers and seating on a carriage supported in guides running along said staple case. A surface of said wedge interacting with said drivers is curvilinear, with lines tangent to the generatrix thereof and a travelling direction of said wedge located so as to constitute an angle varying gradually from 45 deg to zero between a front part of said wedge and the back part thereof in the direction of the wedge travel during stapling procedure.

1 Claim, 4 Drawing Figures

SURGICAL STAPLING APPARATUS

TECHNICAL FIELD

The present invention relates to medical engineering, and, more specifically, to a surgical stapling apparatus.

The surgical stapling apparatus of the present invention can most advantageously be used in suturing gastrointestial organs.

Besides, the surgical stapling apparatus according to the present invention can be used in sutiring the esophagus, lungs, vessels and other organs of human and animal bodies.

BACKGROUND ART

Suturing of tissues and organs representing a basic stage of surgical intervention greatly influences the possibilities and results of surgical operations. At the same time, the stapling procedure largely depends on technical facilities, and, particularly, on the design of the surgical stapling apparatus that would provide a means for making high-quality sutures easily without damaging adjacent tissues and organs, and would permit compensating the growing staple forming forces.

Known in the art is a surgical stapling apparatus (for example, cf. U.S. Pat. No. 3,079,606).

The prior-art surgical stapling apparatus comprises a thrust and a staple cases linked by a sectional joint and a detent. The staple case comprises a working section incorporating staple grooves arranged across a longitudinal axis of the staple case. The staple grooves contain U-shaped staples and staple drivers serving to drive the staples out of the staple grooves during the stapling procedure.

The staple drivers drive the staples by interacting with a pointed wedge adapted to move along the working section of the staple case.

The wedge is arranged at the end of a plate turned toward the working section of the staple case. The other end of the plate mates with a carriage seated in the groove in the staple case and adapted for longitudinal movement therethrough.

The thrust case also incorporates a working section disposed opposite the working section of the staple case. The working section of the thrust case mounts an anvil serving as a thrust receiver of the staples being ejected and bent at the free ends thereof.

For this purpose, the anvil is provided with two rows of sockets disposed along the full length of the thrust case working section opposite the staple grooves in the staple case working section when the stapling apparatus is in the assembled state.

The detent of the staple and thrust cases of the prior art surgical stapling apparatus is devised in the form of a gear rack. In mating the staple and thrust cases, teeth of the gear rack couple in succession and individually lock the working sections relative to each other, and, thus, permit adjusting the suture clearance according to the thickness of biological tissue being joined.

It is known to those skilled in the art that the suture clearance is defined as the distance between the surfaces of the surgical stapling apparatus working sections which interact with biological tissue during the stapling procedure.

In said surgical stapling apparatus, the wedge interacting with the staple drivers is longer than normal because the wedge point point angle appropriate for suturing and resisting the staple forming force may not be more than 15 deg. This feature obstructs making a suture through the full length of the working section because distal ends of the working sections must be long enough to mount the long-size wedge.

There is also known a surgical stapling apparatus (cf. USSR Inventor's Certificate No. 886897) which is the closest analogue to the surgical stapling apparatus of the present invention.

The foregoing surgical stapling apparatus comprises a thrust case and a staple case. The staple case incorporates a lengthwise groove formed by side walls of the working section.

The lengthwise groove accommodates a magazine shaped on the outside identically with the interior of the lengthwise groove. The magazine holds a plurality of U-shaped staples charged evenly in sockets along the full length of the magazine.

The same sockets accommodate staple drivers. Each driver is devised as a right-angle prism, the slant surface whereof faces a magazine bottom surface, and the opposite flat end thereof faces the staples driver thereby.

A handle in assembly with a ring attached to the staple case permits holding the surgical stapling apparatus by the hand. The staple drivers interact with a pointed wedge adapted for movement along the working section of the staple case.

The wedge is mounted at an end of a plate facing the working section of the staple case. The opposite end of the plate is linked with a carriage movable along the groove in the staple case.

The thrust case incorporates a working section disposed opposite the working section of the staple case when the cases are in mated state. A groove provided in a the working section of the thrust case along the full length thereof is formed by side walls of the working section.

The above groove accomodates an anvil incorporating sockets, serving as a thrust receiver of the staples being ejected, and permitting bending the free ends thereof for suturing biological tissue.

A suture clearance adjustment device located in the working section of the thrust case permits moving the anvil in parallel in the direction of the staple case working section, with the result that the suture clearance can be adjusted within a certain range.

The suture clearance adjustment device comprises a crank shaft carrying a knob serving to turn the crankshaft.

The anvil is devised in the form of a right-angle prism, the side surface whereof facing the working section of the staple case and serving to compress biological tissue being sutured incorporates sockets disposed opposite similar sockets in the magazine. A lengthwise groove in the die accommodates a crank of the crankshaft.

When the crankshaft is turned by the knob, the anvil moves toward the working section of the staple case and thus regulates the distance between the cooperation surfaces serving to compress biological tissue, and the working section of the staple case.

The above-mentioned feature of the prior-art surgical stapling apparatus permits adjusting the suture clearance.

The thrust case also carries a handle with a ring which permits holding the case by the hand.

The foregoing surgical stapling apparatus also incorporates a sectional hinge joint and a detent, serving for interconnection of the thrust and staple cases. The sectional hinge joint is disposed in the area of interconnection of the working sections of the staple and thrust cases, and is furnished with a shaft attached to the staple case and introduced into a hole in the thrust case at one end thereof.

The case detent is essentially a double-gear rack disposed beside the handle and ring assemblies.

In the prior-art surgical stapling apparatus, the length of the working sections of the thrust and staple cases is extended to permit arrangement at the distal ends thereof of a long-size wedge having a point angle of not more than 15 deg, and a journal of the crankshaft incorporated in the suture clearance adjustment device.

The above-mentioned relatively high pointing of the wedge, and, hence, the extended length of the working parts of the surgical stapling apparatus are necessary to permit movement of the staple drivers interacting with the wedge, and to permit bending the staples during the suturing procedure.

It has been known (for example, cf. Periodical KHIRURGICHESKIE SSHIVAYUSCHIE APPARATY (Surgical Suturing Apparatus, in Russian), Edition VII, VNIIKHAI, Moscow, 1967, pp.13–15) that the relationship between the staple forming force and the suture clearance depending on the thickness of tissue being joined shows that the staple forming force gradually increases in the region near the minimum suture clearances, and with further reduction of the suture clearances, said force rises abruptly with the result that the operator's effort increases, and, hence, the dimensions of the surgical stapling apparatus working sections must be rather large.

In the prior-art surgical stapling apparatus wherein the wedge point angle is constant, no allowance is made for the nature of growth of forces required to form each staple during the suturing procedure, whereby the surgical stapling apparatus of large size cannot be efficiently used in suturing operative incisions.

The principal object of the present invention is to provide a surgical stapling apparatus, wherein the construction of the wedge will permit reducing the length of the whole surgical stapling apparatus.

Another object of the invention is to provide a surgical stapling apparatus, the construction whereof will improve the service reliability and the operating efficiency thereof in stitching surgical incisions.

A further object of the invention is to provide a surgical stapling apparatus of substantially simplified construction.

With these and other objects in view, a surgical stapling apparatus herein proposed comprises a thrust case and a staple case incorporating a groove formed by the side walls thereof and accommodating a magazine containing staples, staple drivers and a wedge interacting with the staple drivers in ejecting the staples and seating on a carriage supported in guides running along the staple case, with the thrust case furnished with an anvil serving as a thrust receiver of the staples being ejected and bent at the free ends thereof, and also comprises a sectional hinge joint and a sectional detent interconnecting the thrust and staple cases, and a suture clearance adjustment device, wherein, according to the invention, a wedge surface interacting with the staple drivers is curvilinear, with lines tangent to the generatrix thereof and a travelling direction of the wedge located so as to constitute an angle varying gradually from 45 deg to zero between a front part of the wedge and the back part thereof in the direction of the wedge travel during the stapling procedure.

The foregoing wedge surfaces interacting with the drivers are devised so as to permit reducing the wedge length and, hence, the overall dimensions of the working section distal ends extending beyond the suture line, and also to permit reducing the operator's effort.

The above-mentioned angle range from 45 deg to zero is optimum and is determined by the nature of variation of the force required for forming each staple during interaction between the respective staple driver and the wedge curvilinear surface because the forces required for ejecting the staple and piercing the tissue at the initial phase of interaction are not high and are commensurate with the forces normally applied by the operator during movement of the wedge.

At later stages of interaction between the curvilinear surface of the wedge and the staple driver, the staple forming forces are increased and are compensated by the force exerted by the wedge at a respective slope angle between the tangent and the wedge curvilinear surface, which is vertically a wedge point angle in the given area of the curvilinear surface.

Though the staple forming force rises abruptly at the final staple forming stage of the suturing procedure, the operator's effort is not to be increased because the wedge point angle is zero in the wedge back part.

If the angle between the tangent and the wedge curvilinear surface in the front part of the wedge is more than 45 deg, the force to be applied by the operator for moving the wedge will exceed the force required for initial ejection of the staple and for piercing the tissue by the tabs thereof.

If the angle between the tangent and the curvilinear surface in the front part of the wedge is less than 45 deg, the wedge overall length increases, with the result that the dimensions of the working sections of the surgical stapling apparatus must be increased also, whereby difficulties arise in making the sutures along the full length of the surgical stapling apparatus working section and in operating the surgical stapling apparatus in the suture area.

If the angle between the tangent and the curvilinear surface in the back part of the wedge is more than zero, it is impossible to develop a sufficient force exerted by the wedge when a maximum staple forming force is required during the suturing procedure.

If the angle between the tangent and the curvilinear surface in the back part of the wedge is less than zero, that is, if the angle is negative, the staple driver fails to eject the staple when the wedge moves and when the pusher interacts with the wedge, whereby the tissue cannot be pierced by the staple.

The surgical stapling apparatus of the present invention is relatively small-sized, and can be efficiently handled during surgical operations, with the result that jerking and irregular variation of the operator's efforts can be precluded in joining the tissue, and the manipulation of the apparatus introduced into the operative incision can be improved.

The invention will now be described in greater detail with reference to a preferred embodiment thereof taken in conjunction with the accompanying drawings, wherein.

Figure 4:
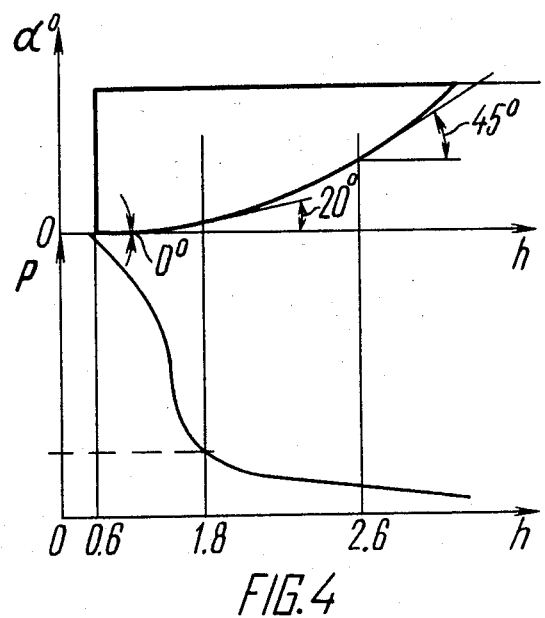

FIG. 4 also shows a graphic relationship between an angle α of incline of a tangent to a wedge surface generatrix and a suture clearance "h" (in mm) as compared to a graphic relationship between a staple forming force P (in kg) and the suture clearance "h" (in mm).

DETAILED DESCRIPTION OF THE INVENTION

Figures 1, 2:
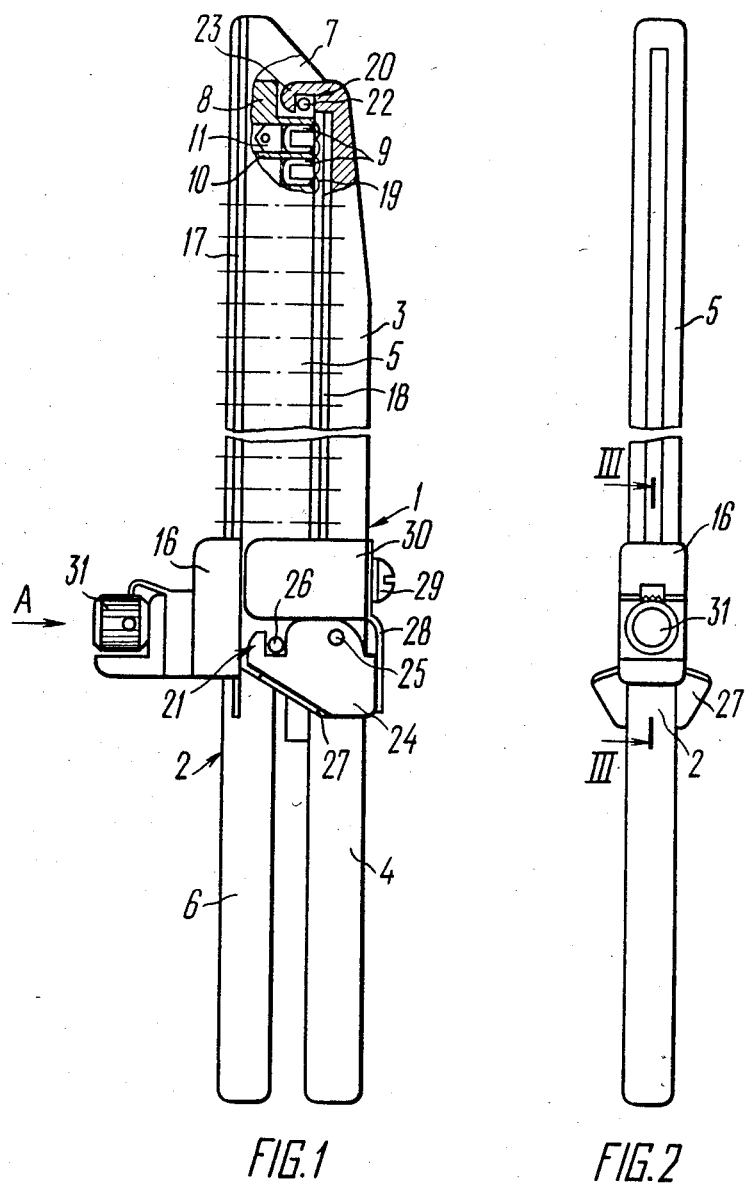
FIG. 1 is a cut-away side view of a surgical stapling apparatus, according to the present invention.
FIG. 2 is a view of same taken along the arrow A of FIG. 1.

Referring now to FIG. 1, a surgical stapling apparatus, according to the present invention, comprises a thrust case 1 and a staple case 2 (FIGS. 1 and 2). The thrust case 1 incorporates a working section 3 (FIG. 1) and a handle 4.

The staple case 2 incorporates a working section 5 and a handle 6. Side walls (not shown) in the staple case 2 form a lengthwise groove 7 running essentially through the full length of the working section 5 of the staple case 2.

The lengthwise groove accommodates a magazine 8 disposed along the full length of the groove and having an outside shape identical to an inside shape of the groove 7. The magazine 8 contains a plurality of U-shaped staples 9 distributed evenly along the full length of the magazine in two rows of sockets (not shown) formed by partitions 10 of the magazine 8.

The magazine 8 accommodates driver 11 of the staples 9 disposed identically to the staples 9 and located between an inside bottom (not shown) of the magazine 8 and the staples 9.

Each driver 11 is devised in the form of a right-angle prism wherein a pointed surface (not shown) faces the bottom of the magazine 8, and an opposite flat end (not shown) faces the staples 9 pushed therewith.

The lengthwise groove 7 accommodates a wedge 12 (FIG. 3) serving for interaction with the drivers 11 of the staples 9. The wedge 12 incorporates a pointed front part 13 and a back part 14, and is furnished with a curvilinear surface 15 interacting with the drivers 11 of the staples 9 during the suturing procedure.

The curvilinear surface 15 of the wedge 12 is machined so that lines tangent to said surface and the travelling direction of the wedge 12 form an angle varying gradually from 45 deg to zero between the pointed part 13 and the back part 14.

The wedge 12 is attached to a carriage 16 (FIG. 1) by any suitable method and is fastened by any traditional devices, not described herein for clarity.

The carriage 16 is supported in guides 17 running along the staple case 2, that is, on outer sides of side walls in said staple case 2 as shown in FIG. 1.

The thrust case 1 comprises an anvil 18 serving as a thrust receiver of the staples 9 being ejected and causes the staples to be bent at the free ends thereof (not shown). For this purpose, the anvil 18 incorporates two rows of sockets 19 disposed all along the working section 3 of the thrust case 1 opposite the sockets of the magazine 8 when the surgical stapling apparatus is in the assembled state.

A sectional hinge joint 20 and a detent 21 serve for interconnecting the thrust case 1 and the staple case 2.

The sectional hinge joint 20 is arranged in distal ends of the working sections 3 and 5. Said sectional hinge joint 20 comprises a fixed shaft 22 attached to the working section 5 of the staple case normal to the side walls thereof, and incorporates a hook 23.

The hook 23 is located on the distal end of the working section 3 in the thrust case 1, and is adapted for catching the shaft 22.

The detent 21 is located in the area where the working sections 3 and 5 curve into the handles 4 and 6. The detent 21 is contrived in the form of a U-shaped plate, the bottom whereof (not shown) is laid upon an outside surface of the thrust case 1 which is opposite to the surface thereof facing the staple case 2. Side parts 24 of the detent 21 embracing side surfaces of the thrust case 1 are seated on a fixed shaft 25 passing through the thrust case 1 normally to the side surfaces thereof.

The side parts 24 form a groove (not shown) accommodating a fixed shaft 26 passing through the staple case 2 normal to the side surfaces thereof. The side parts 24 are provided with flanges 27 (FIGS. 1 and 2) adapted to be pushed by the operator's hand.

The detent 21 also incorporates a plate spring 28 (FIG. 1) held by a screw 29 screwed into the thrust case 1.

Plate stops 30 installed on two sides of the thrust case 1 and located on the side surfaces thereof serve for preventing lateral displacements of the staple case 2 relative to the thrust case 1, that is, in the direction normal to the locating plane of FIG. 1.

The surgical stapling apparatus incorporates a suture clearance adjustment device 31 arranged in the carriage 16 and devised by any conventional method suitable for the purpose and not described herein for clarity.

Figure 3:
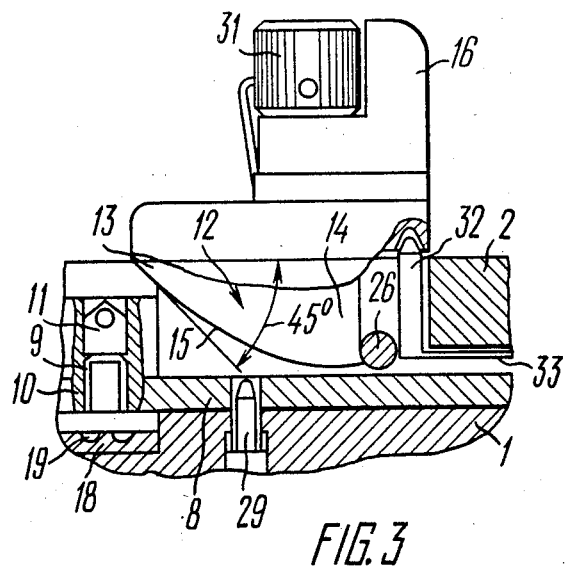
FIG. 3 is an enlarged fragmentary sectional view taken along line III—III of FIG. 2.

Referring now to FIG. 3, the apparatus incorporates a stop 32 serving for locking the carriage 16 in the initial position thereof and devised in the form of a taper pin identified by the same reference number 32, with a spring 33 made integral with the pin 32, the taper end whereof enters a recess in a bottom part of the carriage 16 as shown in FIG. 3.

The surgical stapling apparatus according to the present invention used in suturing of organs and tissue operates as follows.

Prior to use, the surgical stapling apparatus must be inspected to ensure whether the carriage 16 is in its full back position wherein the working section 5 of the staple case 2 is linked with the handle 6 thereof, and is locked by the stop 32. The thrust case 1 must be unmated from the staple case 2.

Then, an appropriate suture clearance must be adjusted by the suture clearance adjustment device 31 according to the thickness of the organ to be stitched.

The working section of the thrust case 1 is to be placed from below under the organ being stitched, for example, under a lung lobe, and is to be located along the line of the interlobal sulcus. The hook 20 is used to seaparate the lung parenchyma in the area where it joins the bronchus, and the hook is then extracted in an upward direction in such a manner as to avoid catching the blood vessels by the hook 20. The lung tissue of the interlobal salcus is placed on the anvil 18 between the hook 20 and the plate stops 30 installed on the working section 3 of the thrust case 1.

The staple case 2 is linked by the sectional hinge joint 20 to the thrust case 1. For this purpose, the shaft 22 attached to the working section 5 of the staple case 2 is introduced into the recess of the hook 23. The staple case 2 and the thrust case 1 are pulled together by the handles 4 and 6 till they are locked in the mated state by the detent 21.

After the cases are coupled, the side parts 24 turn about the shaft 25 to a position where the grooves therein are placed opposite the projecting ends of the shaft 26 in the staple case 2 and where the spring 28 returns them to the initial position thereof, wherein the ends of the shaft 26 are seated in the grooves provided in the side parts 24.

Now the carriage 16 is moved forward along the guides 17 toward the distal end of the staple case 2. While moving, the carriage 16 causes the wedge 12 to travel and to interact with the drivers 11 of the staples 9. The staples 9 are ejected out of the sockets in the magazine 8, and the tabs thereof pierce the suture tissue and join the lung tissue after the ends thereof are bent in the sockets 19 of the anvil 18. At the instant of interaction between the front pointed part 13 of the wedge 12 and the driver 11, the force required for ejection of the staple 9 is not high, with the result that the staple 9 interacting with the curvilinear surface 15 forming an angle of 45 deg with the tangent at this point quickly moves to a position where the tabs thereof are thrust against the sockets 19 of the anvil 18.

As the staple 9 moves farther, the tabs thereof seated in the sockets 19 are caused to bend, and the respective rise of the staple forming force occurs at a section of the curvilinear surface, whereat the angle between the tangent and the curvilinear surface is less than 45 deg. The force required to move the carriage 16 does not vary, and the reduction of the angle between the tangent and the surface 15 results in compensation of the rising staple forming force expressed by the equation.

$$P = F/(tg\alpha),$$

where P is the staple forming force, F is the force required to move the wedge 12 (F=const), and $\alpha$ is the angle between the tangent to the curvilinear surface 15 and the direction of travel of the wedge 12.

FIG. 4 illustrates a graphic relationship between the angle $\alpha$ of incline of the tangent to the generatrix of the curvilinear surface 15 of the wedge 12 and the suture clearance "h" (in mm) as compared to a graphic relationship between the force P (in kg) required for forming the staple 9 and the suture clearance "h" (in mm). Comparison between the above-mentioned relationships clearly shows that said increase in the force of forming the staple 9 occurring during reduction of the suture clearance is accompanied by a decrease in the angle $\alpha$ of incline of the tangent to the curvilinear surface 15, with the result that said increase is compensated, and the force F required for moving the wedge 12 remains constant.

This feature permits adjusting a minimum length of each section of the wedge 12 corresponding to a given force required for forming the staple 9, whereby the total length of the wedge 12 can be substantially reduced, and irregular variation of the operator's efforts can be precluded in stapling work.

A further increase in the force required for forming the staple 9 at a minimum stuture clearance does not lead to an increase in the force to be applied by the operator because the angle of incline of the tangent to the curvilinear surface 15 of the wedge 12 decreases to zero in the back part thereof.

On completion of the stapling procedure, the waste part of the lung lobe is cut off with a scalpel along the side surfaces of the working sections 3 and 5 of the staple case 2 and thrust case 1.

Then the flanges 27 of the detent 21 must be pushed down, and the staple case 2 and thrust case 1 must be unmated by moving the handles 4 and 6 apart.

The sectional hinge joint 20 must be uncoupled to permit extracting the shaft 22 out of the recess in the hook 23, and the surgical stapling apparatus must be removed from the operative incision.

Test samples of the surgical stapling apparatus have been manufactured and tried out, and the advantages of the construction herein proposed have been proved.

The novel construction of the wedge permits twice reducing the length of the staple case working section distal end extending beyond the suture limits, and, hence, permits making a high-quality suture in the lung through the full length of the interlobal sulcus without injuring the adjacent organs, for example, the bronchus.

Since the force to be applied by the operator during the stapling work is reduced, the surgical stapling apparatus of the present invention inserted into the operative incision can be handled easily.

What is claimed is:

1. A surgical stapling apparatus, comprising: a thrust case; a staple case; a lengthwise groove formed by side walls of said staple case; a magazine containing staples and staple drivers and seating in said lengthwise groove; said thrust case incorporating an anvil serving as a thrust receiver of said staples ejected from said magazine and for bending the staples at the free ends thereof; a wedge serving for interaction with said drivers of said staples in said magazine and disposed in said lengthwise groove; guides located along said staple case; a carriage disposed in said guides; said wedge attached to said carriage; said wedge incorporating a surface interacting with said staples of said magazine and shaped curvilinearly whereby lines tangent to the generatrix thereof and a travelling direction of said wedge form an angle varying gradually from 45 deg to zero between the front part thereof and the back part thereof in the wedge travelling direction during the stapling procedure; a sectional hinge joint; a detent; said sectional hinge joint and said detent serving for interconnecting said thrust case and said staple case; and a suture clearance adjustment device.

* * * * *